April 20, 1937. W. G. BATE Plant Pat. 245
ROSE
Filed May 9, 1936
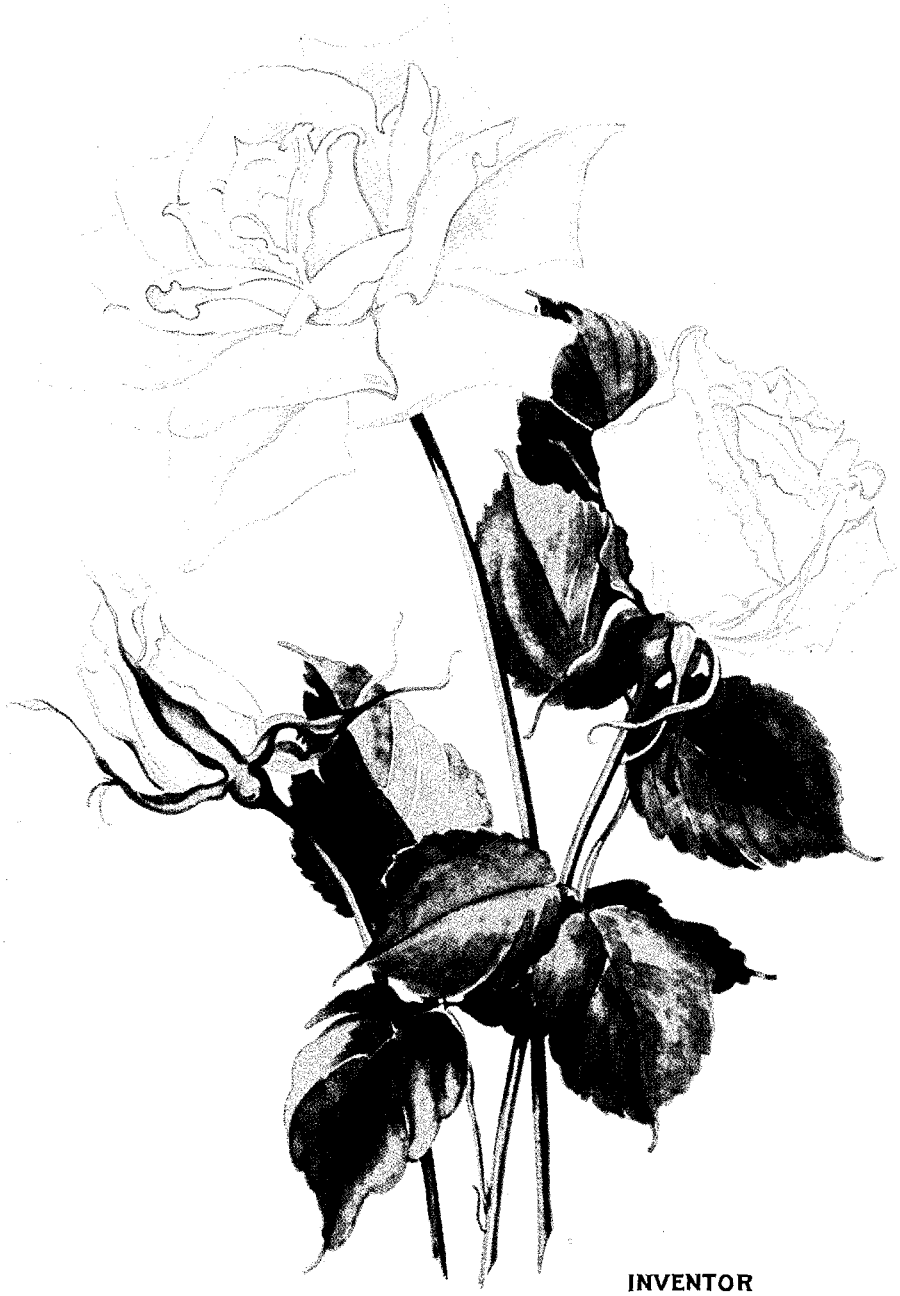
INVENTOR
Warwick G. Bate
BY Frank S. Greene
ATTORNEY Patented Apr. 20, 1937 Plant Pat. 245

UNITED STATES PATENT OFFICE

245

ROSE

Warwick G. Bate, Newton Falls, Ohio

Application May 9, 1936, Serial No. 78,892

1 Claim. (Cl. 47—61)

This discovery relates to a new variety of tea rose which first appeared as a sport of the well known Joanna Hill rose. The new variety of rose discovered and propagated by me has definite characteristics which distinguish it from the parent rose and from all others with which I am familiar.

The most important novel characteristic of the new rose is a peculiar blending and distribution of colors throughout the petals of the flower which causes a progressive variation in shades and colors during the opening of the bud and after the flower is fully opened, an apricot color predominating in the bud and in the newly opened flower which gradually changes as the flower ages until pink becomes the predominant color. Also the distribution of colors in the petals is such as to present different color effects when the flower is viewed from different angles.

Since the discovery of the sport I have succeeded in propagating the new variety and in making permanent the novel and desirable characteristics of the sport plant, and have at the present time a large number of rose plants of the new variety which are producing the flowers herein illustrated and described.

The accompanying illustrations show in full color a bud, a partially opened flower, and a fully opened flower.

The foliage of my new variety of rose is similar to that of the Joanna Hill rose. The leaves are large, dark green and leathery. The stem has relatively few thorns. The plant, however, grows faster and larger, and the flower stems are longer and stronger. The flowers are borne singly on long strong stems and the blooming is profuse and continuous.

The flower is large, having about 50 petals, whereas the Joanna Hill rose has only about 32 petals. The bud is very long and tapering and the petals are large.

Beautiful combinations of colors delicately blended are produced by a peculiar distribution of pigments in the petals. A petal detached from a partially opened flower shows the distribution of colors which produce the varying color effects in the flower. The inner face of an unfaded petal is buttercup yellow at the base (Repertoire de Couleurs, Sheet 22, Plate 1) with faint veins of green immediately adjacent the inner tip. The yellow gradually fades out toward the center of the petal and is not discernible beyond the inner half of the length of the petal. The broad outer part of the inner face of the petal is rosy white (Repertoire de Couleurs, Sheet 8, Plate 1). The gradation from yellow to white is very gradual. In the flower the inner faces of the petals appear to be white at the tips but close inspection shows a pink tinge.

The outer face of the petal is yellow at the inner tip but the yellow is discernible only for a short distance from the tip where it merges into pink, the wide outer portion of the petal being a light pure pink (Repertoire de Couleurs, Sheet 134, Plate 1). In the inner half of the length of the petal the coloration is affected by the yellow, there being a gradual gradation of color from yellow to pink.

In viewing a partially opened flow or a freshly opened flower, the inner faces appear to be creamy white, the creamy effect being probably due to the bright yellow on the inner faces of the petals adjacent the base, and the outer faces appear to have a light apricot color (Repertoire de Couleurs, Sheet 53, Plate 1). Upon very close inspection the pink shade is apparent but viewed from a distance of a few feet the petals appear to have a quite uniform apricot color on their outer faces.

As the petals begin to age the inner faces of the petals become pinker and the pink coloration of the flower becomes more noticeable. The flower appears to change from an apricot shade to a distinctly pink shade. During the fading process the pink pigment appears to flow out toward the tips of the petals leaving the inner end portions of the petals yellow and the outer portions pink. The yellow continues to show more on the inner face of the petal and the pink more on the outer face. When the tips of the petals become dry, the separation of the pink and yellow pigments is practically complete, the major portion of the pink showing on the outer half of the outer face of the petal and the major portion of the yellow showing on the inner half of the inner face of the petal. The terms "creamy white" and "pink" as herein used are to be considered with reference to their ordinary dictionary definitions, and not in connection with the color charts above referred to.

There is a tendency for an uneven distribution of the red and yellow pigments in the outer petals of the bud, which often gives the bud a somewhat mottled appearance, but as the flower opens the spots of deeper color disappear, probably due to the flow of the pink pigment.

The flower of my new rose, by reason of the distribution of colors in the petals and the uniformity of the distribution in all the petals of the flower, gives various delightful color effects when viewed in different lights and from different angles. By reason of the gradual flow of pigment which continues from opening of the bud to the fading of the petals, the color of the rose appears to change decidedly but the coloration continues to be delicate and beautiful.

The flower of my new variety of rose is excellent for the cut flower trade because of its large size, its long, strong stems and its excellent qualities.

I claim:

A rose plant such as that herein shown and described which is characterized by flowers of large size composed of petals colored mainly by yellow and pink pigments, the inner tips of the petals being yellow and the yellow gradually fading from the inner tip to the central portion of the petal, the pink showing almost entirely on the outer face of the petal and being dispersed throughout nearly the entire outer face of the petal in the bud, the color of the inner half of the outer face being modified by the yellow, the pink pigment gradually flowing outwardly away from the yellow during the opening and aging of the flower.

WARWICK G. BATE.